(12) United States Patent
Nakanishi et al.

(10) Patent No.: US 11,399,701 B2
(45) Date of Patent: Aug. 2, 2022

(54) RECEPTACLE MODULE AND MEDICAL DEVICE

(71) Applicant: Sony Olympus Medical Solutions Inc., Tokyo (JP)

(72) Inventors: Tatsuya Nakanishi, Tokyo (JP); Kiyotaka Kanno, Saitama (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 481 days.

(21) Appl. No.: 16/258,978

(22) Filed: Jan. 28, 2019

(65) Prior Publication Data
US 2019/0269303 A1    Sep. 5, 2019

(30) Foreign Application Priority Data
Mar. 5, 2018 (JP) .............................. JP2018-039073

(51) Int. Cl.
*G06F 1/18* (2006.01)
*H05K 9/00* (2006.01)
*A61B 1/00* (2006.01)

(52) U.S. Cl.
CPC .......... *A61B 1/00114* (2013.01); *G06F 1/182* (2013.01); *H05K 9/0007* (2013.01); *H05K 9/0024* (2013.01); *A61B 1/00121* (2013.01)

(58) Field of Classification Search
CPC ..... A61B 1/00124; H01R 9/16; H05K 9/0024
See application file for complete search history.

(56) References Cited

U.S. PATENT DOCUMENTS

2014/0184771 A1* 7/2014 Mazzetti ................... H02J 5/00
                                                                   348/75
2017/0340190 A1* 11/2017 Niwa ................. H01R 13/7033

FOREIGN PATENT DOCUMENTS

| JP | 2-193634 | 7/1990 |
| JP | H09122082 A | 5/1997 |
| JP | 2000279381 A | 10/2000 |
| JP | 2003190085 A | 7/2003 |
| JP | 2014188210 A | 10/2014 |
| JP | 2015173167 A | 10/2015 |
| WO | WO-2016203824 A1 * | 12/2016 ........... H01R 13/652 |

* cited by examiner

*Primary Examiner* — Alexandra L Newton
(74) *Attorney, Agent, or Firm* — Xsensus LLP (57) ABSTRACT

A receptacle module for detachably connecting a connector of a distal end device coming into contact with or inserted into a subject includes: a receptacle substrate including a first surface on which a receptacle to which the connector is detachably connected is mounted, and a second surface on an opposite side of the first surface; a patient circuit unit conducted to the distal end device via the receptacle; and a conductive shielding member mounted on the second surface and configured to shield the patient circuit unit from the opposite side.

7 Claims, 11 Drawing Sheets

RECEPTACLE MODULE AND MEDICAL DEVICE

CROSS-REFERENCE TO RELATED APPLICATION

The present application claims priority to and incorporates by reference the entire contents of Japanese Patent Application No. 2018-039073 filed in Japan on Mar. 5, 2018.

BACKGROUND

The present disclosure relates to a receptacle module and a medical device.

In the related art, there is known a configuration in which a patient circuit is electrically insulated from a secondary circuit in a medical device including a distal end device such as an electronic scope coming into contact with or inserted into a subject (for example, see JP 2-193634 A).

A patient circuit is normally configured as a floating circuit which is not protectively grounded. Therefore, the patient circuit functions as an antenna, and thus noise from the outside to the patient circuit is easily mixed or noise from the patient circuit to the outside is easily transmitted. Therefore, in the medical device (an endoscope imaging device) disclosed in JP 2-193634 A, a patient circuit unit conducted to a distal end device is shielded in a shielding member (a patient circuit unit shielding case) in a patient circuit including the distal end device.

SUMMARY

Figure 16:
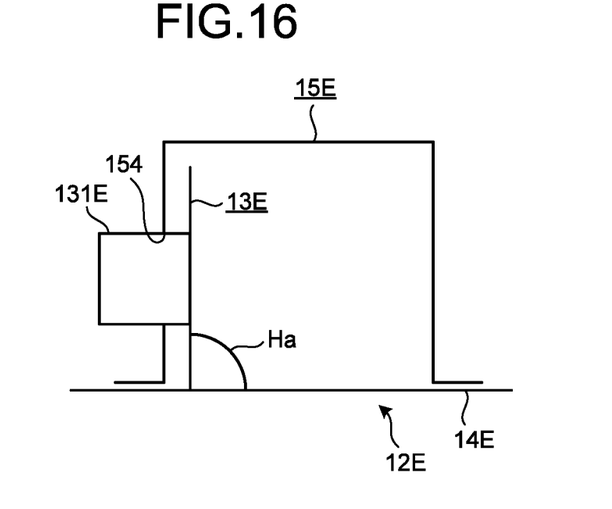
FIG. 16 is a diagram illustrating a problem in a medical device of the related art.
Figure 17:
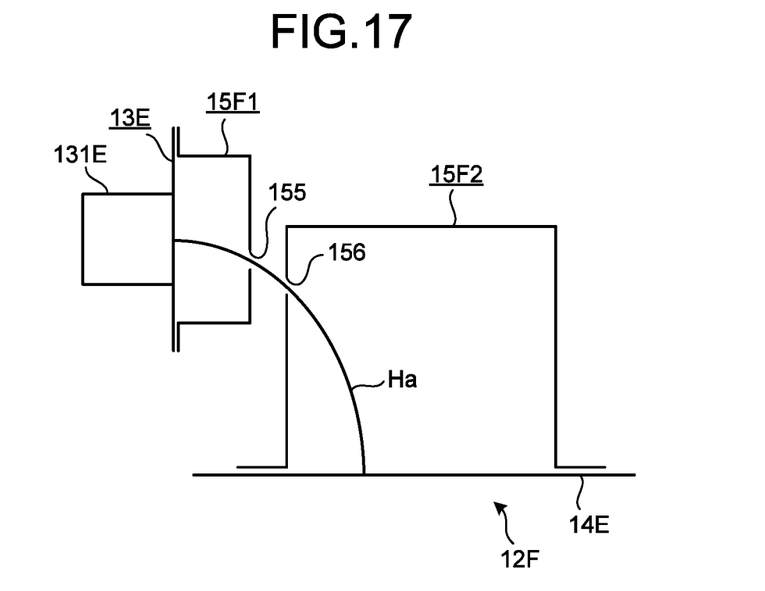
FIG. 17 is a diagram illustrating the problem in the medical device of the related art.

FIGS. 16 and 17 are diagrams illustrating a problem in a medical device of the related art.

Incidentally, when receptacle modules 12E and 12F in which a receptacle 131E detachably connected to a connector of a distal end device such as an electronic scope and a patient substrate 14E are arranged are configured, for example, configurations illustrated in FIGS. 16 and 17 are considered.

The receptacle module 12E illustrated in FIG. 16 includes a receptacle substrate 13E, the patient substrate 14E, and a shielding member 15E.

The receptacle substrate 13E is a printed substrate in which a wiring pattern is provided and the receptacle 131E is mounted to be conducted to the wiring pattern.

The patient substrate 14E is a printed substrate in which a wiring pattern is provided and an electronic component is mounted to be conducted to the wiring pattern. As illustrated in FIG. 16, the patient substrate 14E is disposed at a posture orthogonal to the receptacle substrate 13E. The wiring pattern provided in the patient substrate 14E is conducted to a wiring pattern provided in the receptacle substrate 13E via a harness Ha (FIG. 16).

The wiring pattern provided on the receptacle substrate 13E, the wiring pattern or the electronic component provided on the patient substrate 14E, and the harness Ha function as a patient circuit unit that is conducted to the distal end device in the patient circuit including the distal end device.

The shielding member 15E is formed of a conductive material, has an overall substantially rectangular parallelepiped shape, and has one side surface opened in a container shape. In the shielding member 15E, an opening 154 (FIG. 16) for inserting the receptacle 131E is formed in a side surface of the container shape. As illustrated in FIG. 16, the shielding member 15E is mounted so that the opened portion with the container shape is fitted on a surface on which the wiring pattern or an electronic component is provided on the patient substrate 14E in a state in which the receptacle 131E is inserted through the opening 154, and shields the patient circuit unit.

However, in the configuration illustrated in FIG. 16, the opening 154 is formed in the shielding member 15E. In consideration of an assembly property of the receptacle module 12E, it is necessary to separate the shielding member 15E into two bodies or the like. Therefore, there is a problem that the structure of the shielding member 15E may become complicated.

Accordingly, to simplify the structure of the shielding member 15E, the receptacle module 12F illustrated in FIG. 17 is considered to be adopted.

As illustrated in FIG. 17, the receptacle module 12F includes the receptacle substrate 13E, the patient substrate 14E, and a first shielding member 15F1, and a second shielding member 15F2.

Each of the first shielding member 15F1 and the second shielding member 15F2 is formed of a conductive material, has an overall substantially rectangular parallelepiped shape, and has one side surface opened in a container shape. As illustrated in FIG. 17, the first shielding member 15F1 is mounted so that the opened portion is fitted on an opposite surface of the surface on which the receptacle 131E is mounted on the receptacle substrate 13E and shields a wiring pattern (patient circuit unit) provided on the receptacle substrate 13E. The second shielding member 15F2 is mounted so that the opened portion is fitted on the surface on which the wiring pattern or the electronic component is provided on the patient substrate 14E and shields the wiring pattern or the electronic component (the patient circuit unit) provided in the patient substrate 14E. The wiring pattern provided on the receptacle substrate 13E and the wiring pattern provided on the patient substrate 14E are conducted to each other via the harness Ha (FIG. 17) passing through openings 155 and 156 (FIG. 17) formed in the first shielding member 15F1 and the second shielding member 15F2.

In the configuration illustrated in FIG. 17, however, a part of the harness Ha is located outside the first shielding member 15F1 and the second shielding member 15F2. Therefore, the part of the harness Ha located outside the first shielding member 15F1 and the second shielding member 15F2 functions as an antenna, and thus noise from the outside to the part (the patient circuit unit) of the harness Ha is easily mixed or noise from the part (the patient circuit unit) of the harness Ha to the outside is easily transmitted. That is, there is a problem that a shielding property is inferior.

There is a need for a receptacle module and a medical device capable of improving a shielding property while simplifying a structure.

According to one aspect of the present disclosure, there is provided a receptacle module for detachably connecting a connector of a distal end device coming into contact with or inserted into a subject, the receptacle module including: a receptacle substrate including a first surface on which a receptacle to which the connector is detachably connected is mounted, and a second surface on an opposite side of the first surface; a patient circuit unit conducted to the distal end device via the receptacle; and a conductive shielding member mounted on the second surface and configured to shield the patient circuit unit from the opposite side.

DETAILED DESCRIPTION

Hereinafter, modes for carrying out the present disclosure (hereinafter referred to as embodiments) will be described with reference to the drawings. The present disclosure is not limited to embodiments to be described below. Further, the same reference numerals are given to the same units in the description of the drawings.

Schematic Configuration of Endoscope Device

Figure 1:
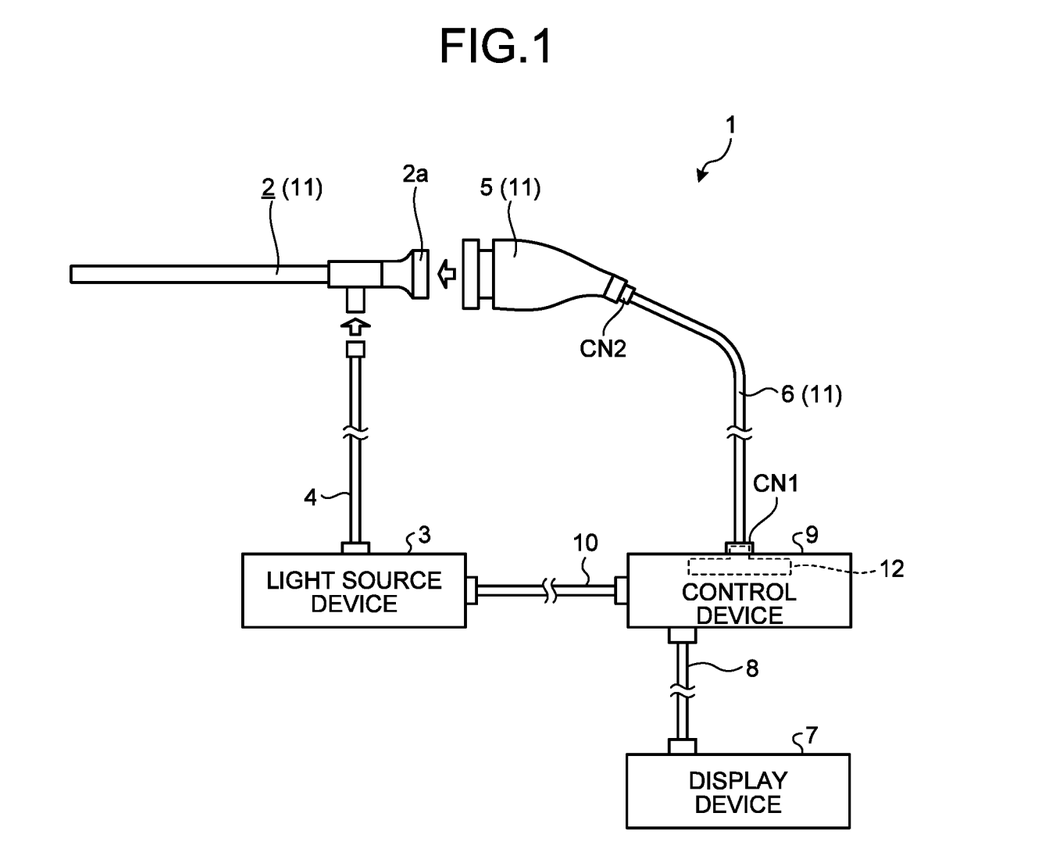
FIG. 1 is a diagram illustrating a schematic configuration of an endoscope device according to an embodiment.

FIG. 1 is a diagram illustrating a schematic configuration of an endoscope device 1 according to an embodiment.

The endoscope device 1 is equivalent to a medical device according to the present disclosure. The endoscope device 1 is used in medical fields and is a device that observes a subject such as the inside of a biological body. The endoscope device 1 includes an insertion unit 2, a light source device 3, a light guide 4, a camera head 5, a first transmission cable 6, a display device 7, a second transmission cable 8, a control device 9, and a third transmission cable 10, as illustrated in FIG. 1.

In the embodiment, the insertion unit 2 is configured as a rigid endoscope. That is, the insertion unit 2 has an elongated shape of which the entirety is rigid or at least a part is flexible and is inserted into a biological body. In the insertion unit 2, an optical system that is configured by one lens or a plurality of lenses and condenses a subject image is provided.

The light source device 3 is connected to one end of the light guide 4 and supplies illumination light for illuminating the biological body to the one end of the light guide 4 under the control of the control device 9.

One end of the light guide 4 is detachably connected to the light source device 3 and the other end of the light guide 4 is detachably connected to the insertion unit 2. Then, the light guide 4 delivers the light supplied from the light source device 3 from the one end to the other end to supply the light to the insertion unit 2. The light supplied to the insertion unit 2 is emitted from the distal end of the insertion unit 2 to be radiated to the inside of the biological body. The light (subject image) radiated to the biological body and reflected from the biological body is condensed by the optical system inside the insertion unit 2.

The camera head 5 is detachably connected to a proximal end (an eyepiece 2a (FIG. 1)) of the insertion unit 2. The camera head 5 captures a subject image condensed in the insertion unit 2 and outputs an image signal (RAW signal) obtained through the imaging under the control of the control device 9. In the embodiment, the image signal is an image signal with 4K or more.

The first transmission cable 6 includes connectors CN1 and CN2 at both ends, the connector CN1 (FIG. 1) at one end is detachably connected to the control device 9, and the connector CN2 (FIG. 1) at the other end is detachably connected to the camera head 5. In addition, the first transmission cable 6 transmits an image signal output from the camera head 5 to the control device 9 and transmits a control signal, a synchronization signal, a clock, driving power, and the like output from the control device 9 to the camera head 5.

The transmission of the image signal from the camera head 5 to the control device 9 via the first transmission cable 6 may be transmission of the image signal realized by an optical signal or may be transmission of an image signal realized by the electric signal. The same applies to the transmission of the control signal, the synchronization signal, and the clock from the control device 9 to the camera head 5 via the first transmission cable 6.

The insertion unit 2, the camera head 5, and the first transmission cable 6 described above are equivalent to a distal end device 11 (FIG. 1) according to the present disclosure.

The control device 9 includes a central processing unit (CPU) and the like and comprehensively controls operations of the light source device 3, the camera head 5, and the display device 7.

Specifically, the control device 9 generates a video signal by performing a predetermined process on the image signal acquired from the camera head 5 via the first transmission cable 6 and outputs the video signal to the display device 7 via the second transmission cable 8. Then, the display device 7 displays an image based on the video signal. The control device 9 outputs a control signal or the like to the camera head 5 or the light source device 3 via the first transmission cable 6 and the third transmission cable 10.

The above-described control device 9 includes a receptacle module 12 (FIG. 1) to which the connector CN1 of the distal end device 11 is detachably connected. The detailed configuration of the receptacle module 12 will be described later.

One end of the third transmission cable 10 is detachably connected to the light source device 3 and the other end thereof is detachably connected to the control device 9. Then, the third transmission cable 10 transmits a control signal from the control device 9 to the light source device 3.

Primary Circuit, Secondary Circuit, and Patient Circuit

Figure 2:
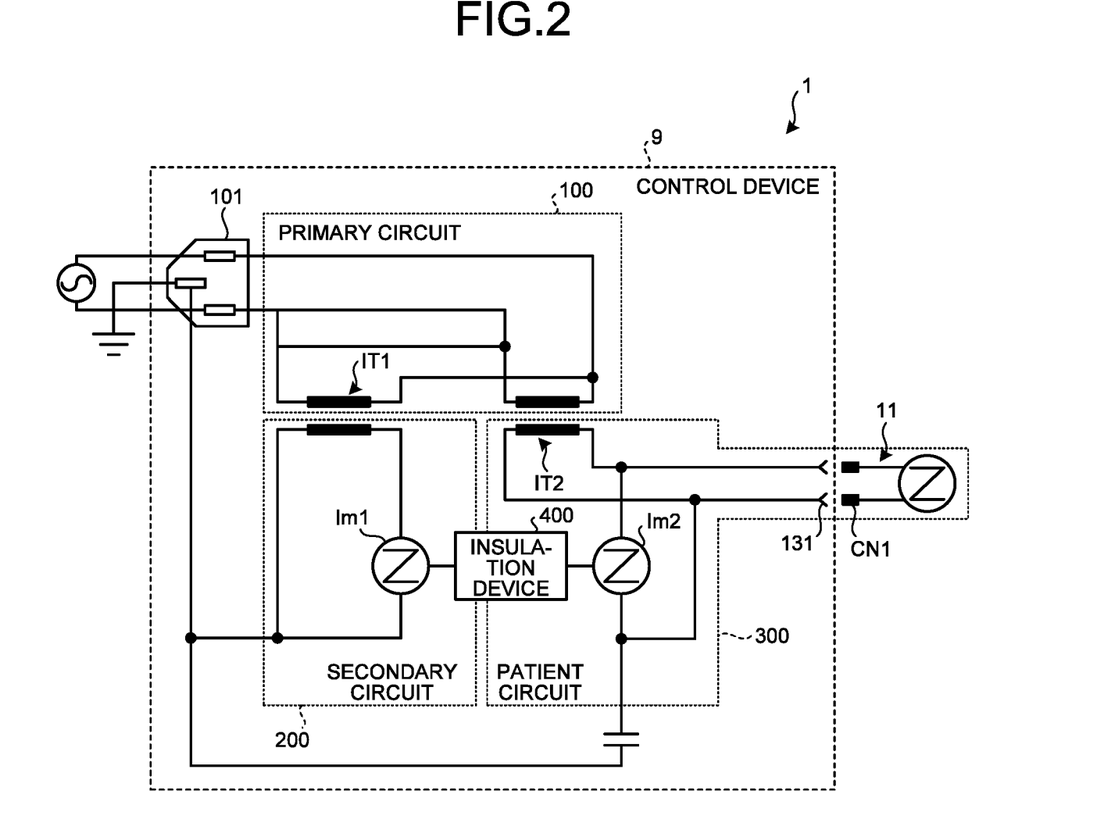
FIG. 2 is a diagram illustrating examples of a primary circuit, a secondary circuit, and a patient circuit in the endoscope device.

FIG. 2 is a diagram illustrating a primary circuit 100, a secondary circuit 200, and a patient circuit 300 in the endoscope device 1.

In the above-described endoscope device 1, as illustrated in FIG. 2, three circuits (the primary circuit 100, the secondary circuit 200, and the patient circuit 300) are broadly provided.

The primary circuit 100 is provided inside the control device 9 and is connected to a commercial power supply via an inlet 101. Then, the primary circuit 100 performs power supply to each of the secondary circuit 200 and the patient circuit 300.

The secondary circuit 200 is provided inside the control device 9 and includes, for example, a signal processor (not illustrated) that performs a predetermined process on an image signal acquired from the camera head 5 and the like. The secondary circuit 200 is supplied with power from the primary circuit 100 via a first insulation transformer IT1 (FIG. 2). That is, the primary circuit 100 is electrically insulated from the secondary circuit 200. The secondary circuit 200 is protectively grounded.

The patient circuit 300 is an electric circuit for which a biological body itself serves as a part of the circuit when the distal end device 11 comes into contact with the biological body, is provided inside the distal end device 11 and the control device 9, and includes, for example, an image sensor (not illustrated) that captures a subject image condensed in the insertion unit 2, or the like. The patient circuit 300 is supplied with power from the primary circuit 100 via a second insulation transformer IT2 (FIG. 2). That is, the primary circuit 100 is electrically insulated from the patient circuit 300. In addition, the patient circuit 300 is electrically insulated from the secondary circuit 200. Further, the secondary circuit 200 and the patient circuit 300 are connected to an insulation device 400 via a first impedance element Im1 provided in the secondary circuit 200 and a second impedance element Im2 provided in the patient circuit 300.

Here, as the first impedance element Im1 and the second impedance element Im2, capacitors, coils, resistors, or the like may be exemplified. As the insulation device 400, for example, a photocoupler, a high-frequency transformer, or the like may be exemplified. Between the patient circuit 300 and the secondary circuit 200, an image signal, a control signal, a synchronization signal, a clock, and the like are transmitted via the insulation device 400.

Configuration of Receptacle Module

Figure 3:
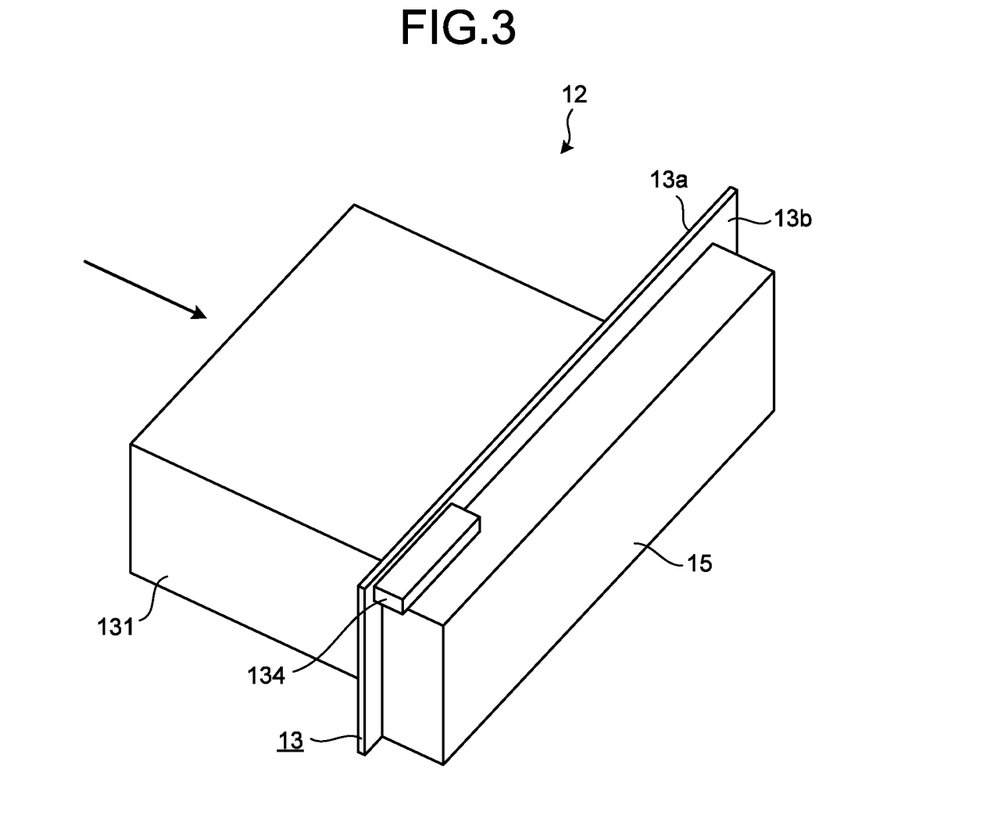
FIG. 3 is a diagram illustrating a receptacle module.
Figure 4:
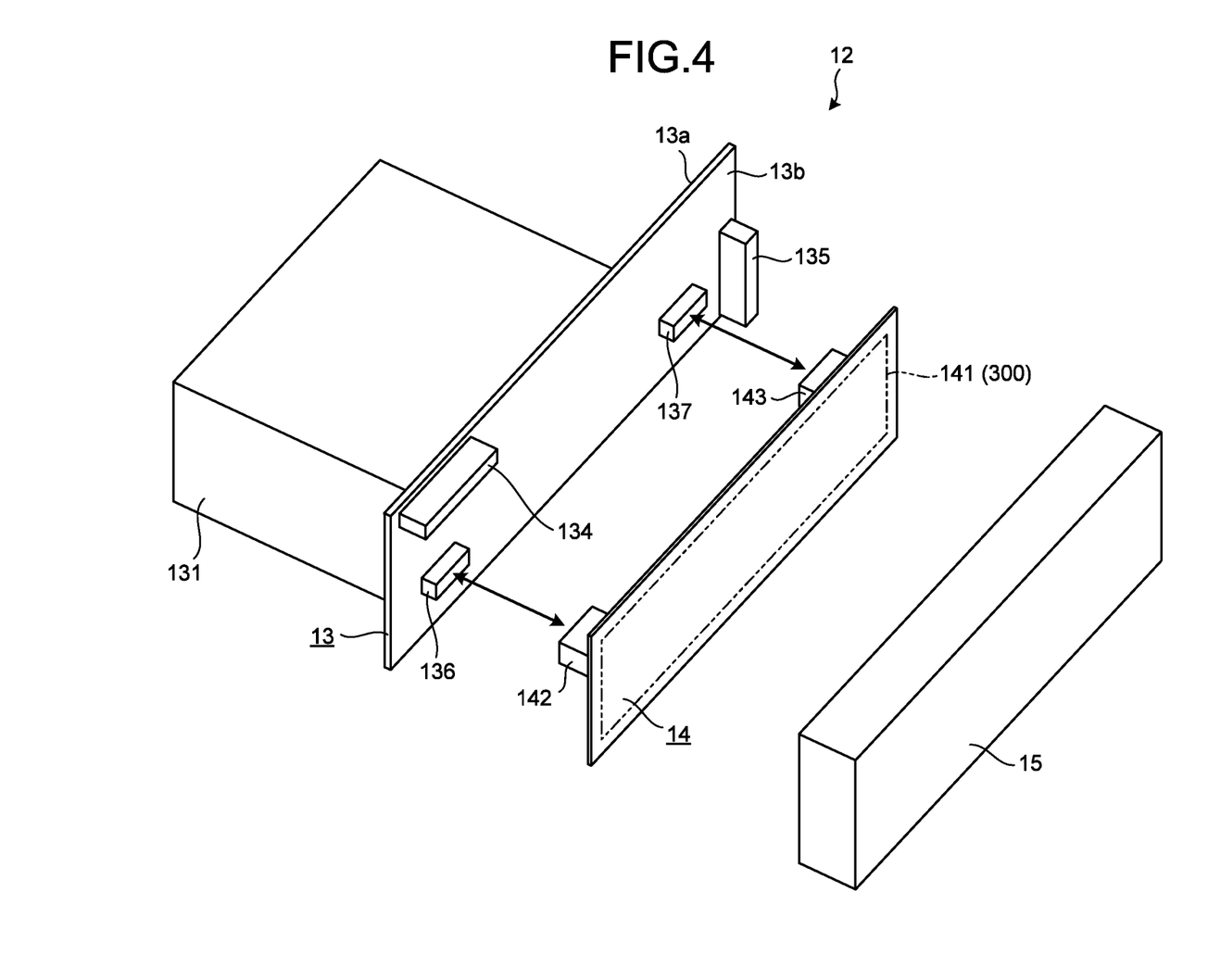
FIG. 4 is a diagram illustrating the receptacle module.
Figure 5:
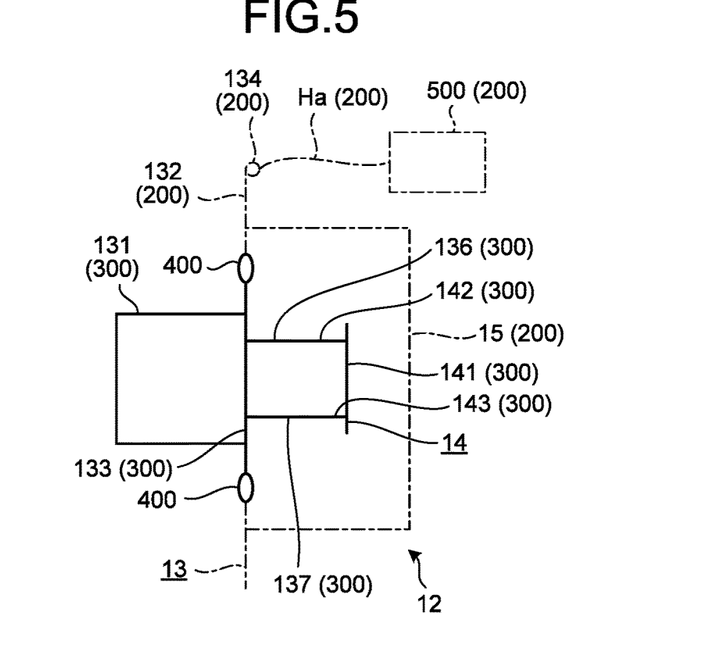
FIG. 5 is a diagram illustrating the receptacle module.

FIGS. 3 to 5 are diagrams illustrating the receptacle module 12. Specifically, FIG. 3 is a perspective view illustrating the overall receptacle module 12. FIG. 4 is an exploded perspective view illustrating the receptacle module 12 illustrated in FIG. 3. FIG. 5 is a diagram illustrating the receptacle module 12 when viewed from the side and is a diagram schematically illustrating the inside of the shielding member 15. An arrow illustrated in FIG. 3 indicates an insertion direction of the connector CN1 into a receptacle 131. In FIG. 5, to facilitate the description, the patient circuit 300 and the insulation device 400 are indicated by solid lines, the secondary circuit 200 is illustrated by a one-dot chain line, and a second connection connector 135 is not illustrated.

The receptacle module 12 includes a receptacle substrate 13, a patient substrate 14 (FIGS. 4 and 5), and the shielding member 15, as illustrated in FIGS. 3 to 5.

Figure 6:
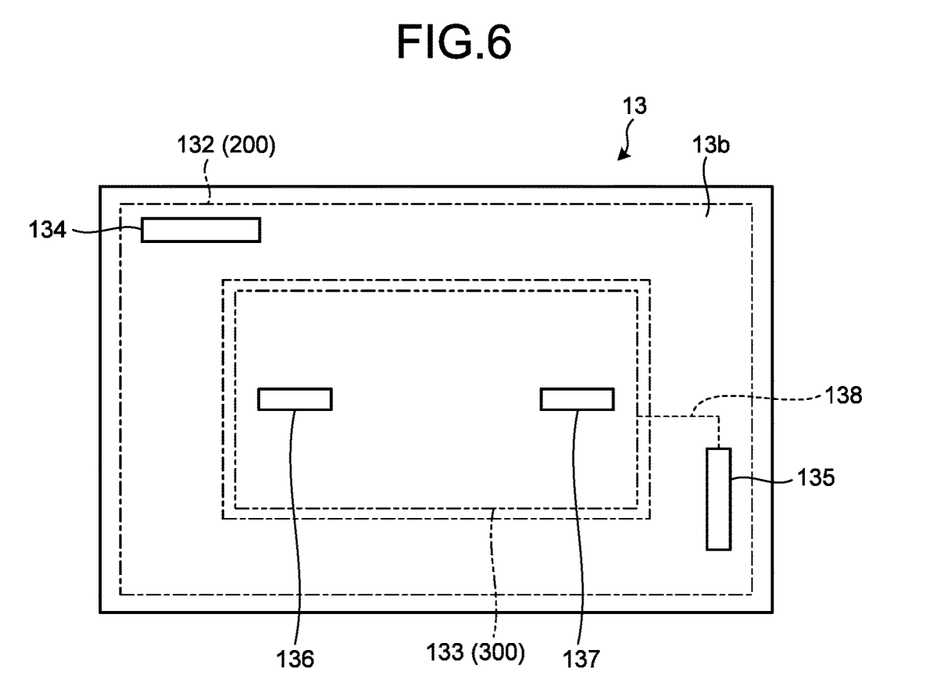
FIG. 6 is a diagram illustrating a receptacle substrate.

FIG. 6 is a diagram illustrating the receptacle substrate 13. Specifically, FIG. 6 is diagram illustrating the receptacle substrate 13 when viewed from the side of a surface 13b opposite to a surface 13a on which the receptacle 131 is mounted.

The receptacle substrate 13 is formed of an insulation material such as a glass epoxy resin and is a plate that is rectangular in plan view. As illustrated in FIG. 6, a first secondary circuit unit 132 and a first patient circuit unit 133 are provided on the receptacle substrate 13. In the embodiment, the receptacle substrate 13 is configured as a multi-layer printed substrate.

The first secondary circuit unit 132 is provided in a region that has a rectangular frame shape extending along an outer edge of the receptacle substrate 13, as illustrated in FIG. 6. The first secondary circuit unit 132 is configured in a wiring pattern that functions as a signal line, a wiring pattern that functions as a ground line, or the like and forms a part of the secondary circuit 200. That is, the first secondary circuit unit 132 is equivalent to a secondary circuit unit according to the present disclosure. The first secondary circuit unit 132 (mainly a ground line of the first secondary circuit unit 132) is equivalent to a shielding pattern according to the present disclosure.

The first patient circuit unit 133 is configured in a wiring pattern that functions as a signal line, a wiring pattern that functions as a ground line, or the like and is provided in a layer closer to the side of the surface 13b than the first secondary circuit unit 132 in the receptacle substrate 13. The first patient circuit unit 133 is provided in a middle region surrounded by the first secondary circuit unit 132, as illustrated in FIG. 6. The first patient circuit unit 133 forms a part of the patient circuit 300. The receptacle 131 is mounted on the surface 13a of the receptacle substrate 13 to be conducted to the first patient circuit unit 133.

The first secondary circuit unit 132 and the first patient circuit unit 133 are connected to the insulation device 400 (FIG. 5) mounted on the receptacle substrate 13 in an electrically insulated state.

A first connection connector 134 to a fourth connection connector 137 are mounted on the surface 13b of the receptacle substrate 13, as illustrated in FIG. 3, 4, or 6.

As illustrated in FIG. 6, the first connection connector 134 is mounted on the surface 13b in a region overlapping the first secondary circuit unit 132 in a planar manner and is conducted to the first secondary circuit unit 132. A secondary circuit substrate 500 (FIG. 5) on which other secondary circuits other than the first secondary circuit unit 132 are provided in the secondary circuit 200 is connected to the first connection connector 134 via a harness Ha (FIG. 5) or the like.

As illustrated in FIG. 6, the second connection connector 135 is mounted on the surface 13b in a region overlapping the first secondary circuit unit 132 in a planar manner and is conducted to the first patient circuit unit 133 via a wiring pattern 138 such as a copper foil provided on the receptacle substrate 13. The wiring pattern 138 is provided in a layer closer to the side of the surface 13b than the first secondary circuit unit 132. The second connection connector 135 is connected to the second insulation transformer IT2 via a harness (not illustrated) or the like. That is, the patient circuit 300 is supplied with power via the second connection connector 135.

As illustrated in FIG. 6, a third connection connector 136 and a fourth connection connector 137 are mounted on the surface 13b in regions overlapping the first patient circuit unit 133 in a planar manner and are each conducted to the first patient circuit unit 133. Then, the third connection connector 136 and the fourth connection connector 137 are configured as B-to-B connectors and are connected to the patient substrate 14.

In the above-described receptacle substrate 13, as long as the first secondary circuit unit 132 (the secondary circuit 200) is electrically insulated from the first patient circuit unit 133 and the wiring pattern 138 (the patient circuit 300), the first secondary circuit unit 132, the first patient circuit unit 133, and the wiring pattern 138 may not be provided in different layers and may be provided in the same layer. The receptacle substrate 13 may be configured as a monolayer printed substrate rather than a multilayer printed substrate.

The patient substrate 14 is formed of an insulation material such as a glass epoxy resin and is a plate which has a planar size smaller than the receptacle substrate 13 and is rectangular in plan view. As illustrated in FIG. 4, a second patient circuit unit 141 is provided on the patient substrate 14.

The second patient circuit unit 141 includes a wiring pattern that functions as a signal line, a wiring pattern that functions as a ground line, an electronic component that is conducted to these wiring patterns, and the like and forms a part of the patient circuit 300.

The first patient circuit unit 133 and the second patient circuit unit 141 described above are equivalent to a patient circuit unit according to the present disclosure.

A fifth connection connector 142 and a sixth connection connector 143 (FIG. 4) that are configured as B-to-B connectors and are electrically connected to the third connection connector 136 and the fourth connection connector 137, respectively, are mounted on the patient substrate 14. The fifth connection connector 142 and the sixth connection connector 143 are mounted in regions overlapping the second patient circuit unit 141 in a planar manner and are conducted to the second patient circuit unit 141. That is, the first patient circuit unit 133 and the second patient circuit unit 141 are conducted to each other via the third to sixth connection connectors 136, 137, 142, and 143.

As described above, in the present embodiment, the patient substrate 14 is disposed on the receptacle substrate 13 at a posture facing the surface 13b.

The shielding member 15 is formed of a conductive material, has an overall substantially rectangular parallelepiped shape, and has one side surface opened in a container shape. As illustrated in FIGS. 3 to 5, the shielding member 15 is mounted on the surface 13b of the receptacle substrate 13 in a region in which the opened portion is overlapped the first secondary circuit unit 132 in a planar manner (is mounted to surround the first patient circuit unit 133) and is conducted to the ground line of the first secondary circuit unit 132. That is, the shielding member 15 is set to a reference potential of the secondary circuit 200. Then, the shielding member 15 shields the first patient circuit unit 133 and the second patient circuit unit 141 from the side of the surface 13b. The shielding member 15 surrounds the first patient circuit unit 133 and the second patient circuit unit 141 between the shielding member 15 and the receptacle substrate 13 (mainly the ground line (a shielding pattern according to the present disclosure) of the first secondary circuit unit 132). At this time, the insulation device 400 and the third to sixth connection connectors 136, 137, 142, and 143 are also surrounded by the receptacle substrate 13 and the shielding member 15. On the other hand, the first connection connector 134 and the second connection connector 135 are located outside the shielding member 15.

According to the above-described embodiment, the following advantage may be obtained.

In the receptacle module 12 according to the embodiment, the structure in which the shielding member 15 is mounted on the surface 13b of the receptacle substrate 13 and the shielding member 15 shields the first patient circuit unit 133 and the second patient circuit unit 141 is adopted.

Therefore, it is possible to achieve the advantage that it is not necessary to separate the shielding member 15 into two bodies or the like and the structure of the shielding member 15 may thus be simplified. As a result, it is possible to improve an assembly property of the receptacle module 12 and reduce manufacturing cost. By simplifying the structure of the shielding member 15, it is possible to achieve miniaturization and a reduction in the weight of the receptacle module 12.

In particular, the patient circuit according to the present disclosure is separated into two units: the first patient circuit unit 133 provided on the receptacle substrate 13 and the second patient circuit unit 141 provided on the patient substrate 14. Therefore, for example, it is possible to reduce the size of the single receptacle substrate 13 or patient substrate 14, compared to a configuration in which all the patient circuit units are provided on the receptacle substrate 13.

In the receptacle module 12 according to the embodiment, the shielding member 15 is set to the reference potential of the secondary circuit 200.

Therefore, since the shielding member 15 is set to the reference potential of the protectively grounded secondary circuit 200, the first patient circuit unit 133 and the second patient circuit unit 141 may be stably shielded (electromagnetically shielded).

In the receptacle module 12 according to the embodiment, the first secondary circuit unit 132 (mainly the ground line of the first secondary circuit unit 132) is caused to function as a shielding pattern according to the present disclosure.

Therefore, the first patient circuit unit 133 and the second patient circuit unit 141 are surrounded in the shielding member 15 and the first secondary circuit unit 132 (mainly the ground line of the first secondary circuit unit 132), and thus it is possible to further improve the shielding property of the first patient circuit unit 133 and the second patient circuit unit 141.

Other Embodiments

The modes for carrying out the present disclosure have been described above, but the present disclosure is not limited to only the above-described embodiments.

Figure 7:
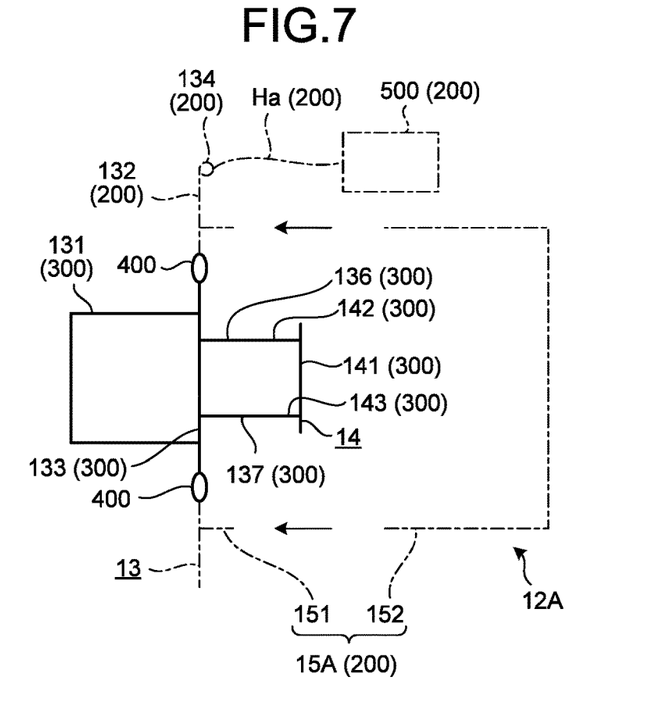
FIG. 7 is a diagram illustrating a first modification example of the embodiment.

FIG. 7 is a diagram illustrating a first modification example of the embodiment. Specifically, FIG. 7 is a diagram corresponding to FIG. 5. In FIG. 7, as in FIG. 5, the patient circuit 300 and the insulation device 400 are indicated by solid lines, the secondary circuit 200 is illustrated by a one-dot chain line, and the second connection connector 135 is not illustrated.

In the above-described embodiment, instead of the receptacle module 12, a receptacle module 12A according to the first modification example illustrated in FIG. 7 may be adopted.

In the receptacle module 12A, a shielding member 15A that has a different structure from the shielding member 15 is adopted unlike the receptacle module 12 described in the above-described embodiment.

Specifically, the shielding member 15A includes a base unit 151 and a shielding case 152, as illustrated in FIG. 7.

The base unit 151 is formed of a conductive material and has a rectangular frame shape. Then, the base unit 151 is mounted on the surface 13b of the receptacle substrate 13 in a region overlapping the first secondary circuit unit 132 in a planar manner (is mounted to surround the first patient circuit unit 133) and is conducted to the ground line of the first secondary circuit unit 132.

The shielding case 152 is formed of a conductive material, has an overall substantially rectangular parallelepiped shape, and has one side surface opened in a container shape. The shielding case 152 is connected to the base unit 151 so that the opened portion is detachably mounted by a snap-fit, a screw, or the like. In a state in which the shielding case 152 is mounted on the base unit 151, the shielding member 15A surrounds the first patient circuit unit 133, the second patient circuit unit 141, the insulation device 400, and the third to sixth connection connectors 136, 137, 142, and 143 between the shielding member 15A and the receptacle substrate 13 (mainly the ground line (a shielding pattern according to the present disclosure) of the first secondary circuit unit 132) in a state in which the shielding member 15A is set to the reference potential of the secondary circuit 200, as in the above-described embodiment. On the other hand, the first connection connector 134 and the second connection connector 135 are located outside the shielding member 15A as in the above-described embodiment.

According to the above-described first modification example, it is possible to obtain the following advantage in addition to the same advantages as those of the above-described embodiment.

In the receptacle module 12A according to the first modification example, the shielding member 15A includes the base unit 151 and the shielding case 152 connected to each other by a snap-fit, a screw, or the like. Therefore, it is possible to further improve the assembly property of the receptacle module 12.

Figure 8:
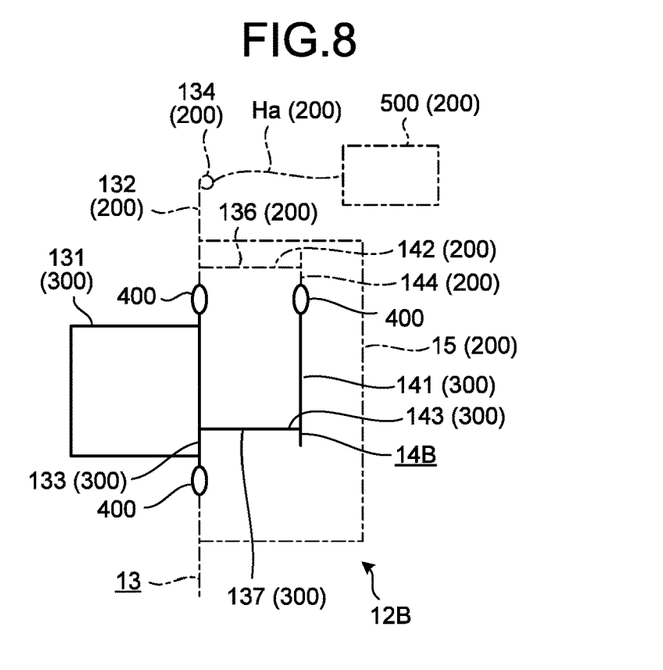
FIG. 8 is a diagram illustrating a second modification example of the embodiment.

FIG. 8 is a diagram illustrating a second modification example of the embodiment. Specifically, FIG. 8 is a diagram corresponding to FIG. 5. In FIG. 8, as in FIG. 5, the patient circuit 300 and the insulation device 400 are indicated by solid lines, the secondary circuit 200 is illustrated by a one-dot chain line, and the second connection connector 135 is not illustrated.

In the above-described embodiment, instead of the receptacle module 12, a receptacle module 12B according to the second modification example illustrated in FIG. 8 may be adopted.

In the receptacle module 12B, unlike the receptacle module 12 described in the above-described embodiment, a patient substrate 14B of which a mounting position of the third connection connector 136 is different and which has a different configuration from the patient substrate 14 is adopted.

Specifically, the third connection connector 136 is mounted on the surface 13b of the receptacle substrate 13 in a region overlapping the first secondary circuit unit 132 in a planar manner and is conducted to the first secondary circuit unit 132, as illustrated in FIG. 8.

As illustrated in FIG. 8, a second secondary circuit unit 144 is provided on the patient substrate 14B unlike the patient substrate 14 described in the above-described embodiment.

The second secondary circuit unit 144 includes a wiring pattern that functions as a signal line, a wiring pattern that functions as a ground line, an electronic component that is conducted to these wiring patterns, and the like, and forms a part of the secondary circuit 200. The second patient circuit unit 141 and the second secondary circuit unit 144 are connected to the insulation device 400 (FIG. 8) mounted on the patient substrate 14B in an electrically insulated state. The fifth connection connector 142 is mounted in a region overlapping the second secondary circuit unit 144 in a planar manner and is conducted to the second secondary circuit unit 144. That is, the first secondary circuit unit 132 and the second secondary circuit unit 144 are conducted to each other via the third connection connector 136 and the fifth connection connector 142. On the other hand, the first patient circuit unit 133 and the second patient circuit unit 141 are conducted to each other via the fourth connection connector 137 and the sixth connection connector 143.

In a state in which the shielding member 15 is set to the reference potential of the secondary circuit 200, the shielding member 15 surrounds the first patient circuit unit 133, the second patient circuit unit 141, the second secondary circuit unit 144, the insulation device 400, and the third to sixth connection connectors 136, 137, 142, and 143 with the receptacle substrate 13 (mainly the ground line (a shielding pattern according to the present disclosure) of the first secondary circuit unit 132). On the other hand, the first connection connector 134 and the second connection connector 135 are located outside the shielding member 15 as in the above-described embodiment.

Even when the second secondary circuit unit 144 is provided in the patient substrate 14B as in the above-described second modification example, it is possible to obtain the same advantages as those of the above-described embodiment.

Figure 9:
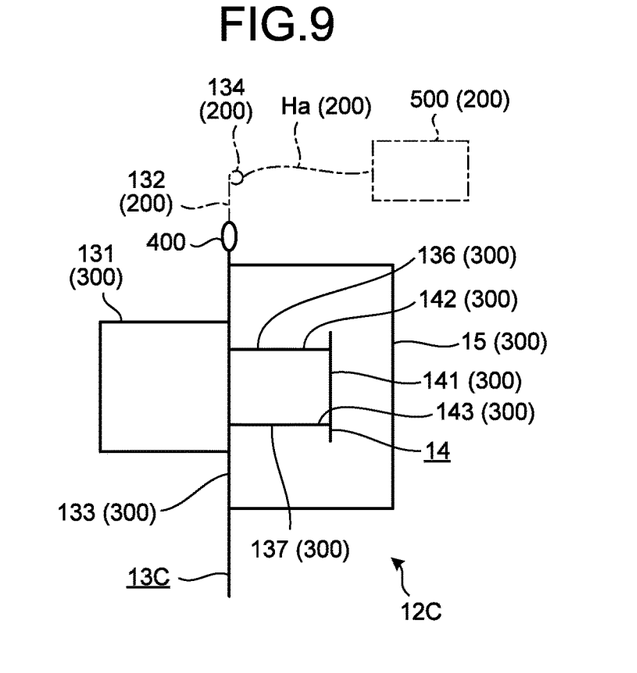
FIG. 9 is a diagram illustrating a third modification example of the embodiment.
Figure 10:
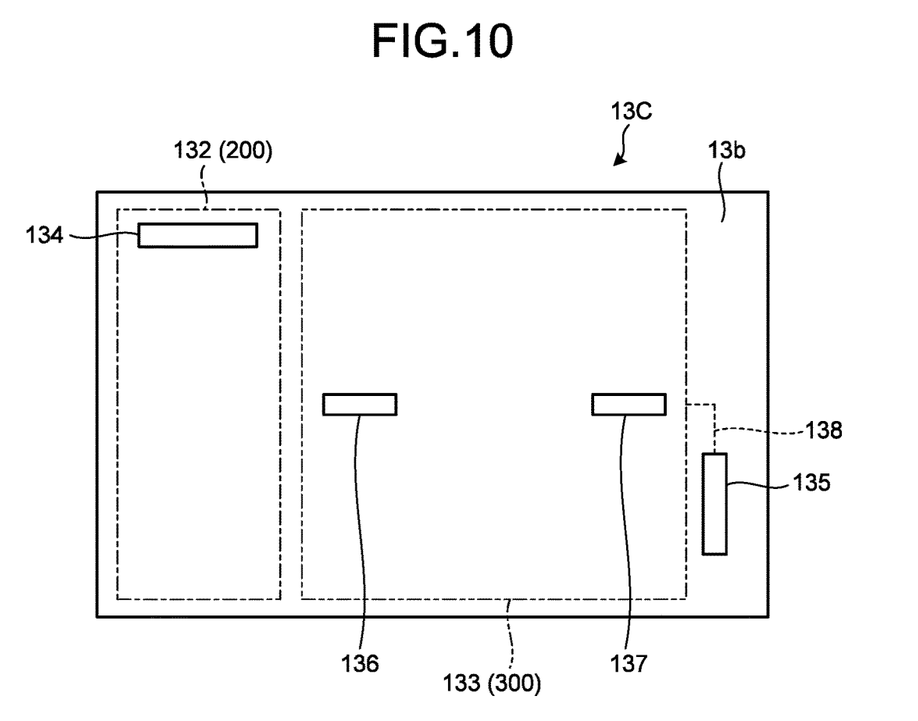
FIG. 10 is a diagram illustrating the third modification example of the embodiment.

FIGS. 9 and 10 are diagrams illustrating a third modification example of the embodiment. Specifically, FIG. 9 is a diagram corresponding to FIG. 5. In FIG. 9, as in FIG. 5, the patient circuit 300 and the insulation device 400 are indicated by solid lines, the secondary circuit 200 is illustrated by a one-dot chain line, and the second connection connector 135 is not illustrated. FIG. 10 is a diagram corresponding to FIG. 6.

In the above-described embodiment, instead of the receptacle module 12, a receptacle module 12C according to the third modification example illustrated in FIG. 9 may be adopted.

In the receptacle module 12C, unlike the receptacle module 12 described in the above-described embodiment, a receptacle substrate 13C which has a different configuration from the receptacle substrate 13 is adopted and a mounting position of the shielding member 15 is different.

Specifically, the receptacle substrate 13C has different regions in which the first secondary circuit unit 132 and the first patient circuit unit 133 are formed from the receptacle substrate 13 described in the above-described embodiment, as illustrated in FIG. 10.

As illustrated in FIG. 10, when the receptacle substrate 13C is divided into two regions, that is, a left rectangular region and a right rectangular region in plan view, the first secondary circuit unit 132 is provided in the left rectangular region. On the other hand, the first patient circuit unit 133 is provided in the right rectangular region. The second connection connector 135 is mounted on the surface 13b of the receptacle substrate 13C in a region deviating from the first patient circuit unit 133 in a plan view and is conducted to the first patient circuit unit 133 via the wiring pattern 138. The third connection connector 136 and the fourth connection connector 137 are mounted on the surface 13b in regions overlapping the first patient circuit unit 133 in a planar manner and are conducted to the first patient circuit unit 133 as in the above-described embodiment.

As illustrated in FIG. 9, the shielding member 15 is mounted on the surface 13b of the receptacle substrate 13C in a region in which the opened portion is overlapped the first patient circuit unit 133 in a planar manner (the right rectangular region illustrated in FIG. 10) and is conducted to the ground line of the first patient circuit unit 133. That is, the shielding member 15 is set to the reference potential of the patient circuit 300. The shielding member 15 surrounds mainly the signal line of the first patient circuit unit 133, the second patient circuit unit 141, and the third to sixth connection connectors 136, 137, 142, and 143 between the shielding member 15 and the receptacle substrate 13C (mainly the ground line (a shielding pattern according to the present disclosure) of the first patient circuit unit 133). On the other hand, the insulation device 400, the first connection connector 134, and the second connection connector 135 are located outside the shielding member 15.

According to the above-described third modification example, it is possible to obtain the following advantage in addition to the same advantages as those of the above-described embodiment.

In the receptacle module 12C according to the third modification example, the shielding member 15 is set to the reference potential of the patient circuit 300.

Therefore, in the receptacle substrate 13C, it is not necessary to provide the first secondary circuit unit 132 so that the first patient circuit unit 133 is surrounded in a planar manner. Therefore, it is possible to improve the degree of freedom of design of the receptacle substrate 13C. In the receptacle substrate 13C, it is possible to simplify the structure in which the first secondary circuit unit 132 is electrically insulated from the first patient circuit unit 133. Therefore, it is possible to achieve miniaturization of the receptacle substrate 13C.

Figure 11:
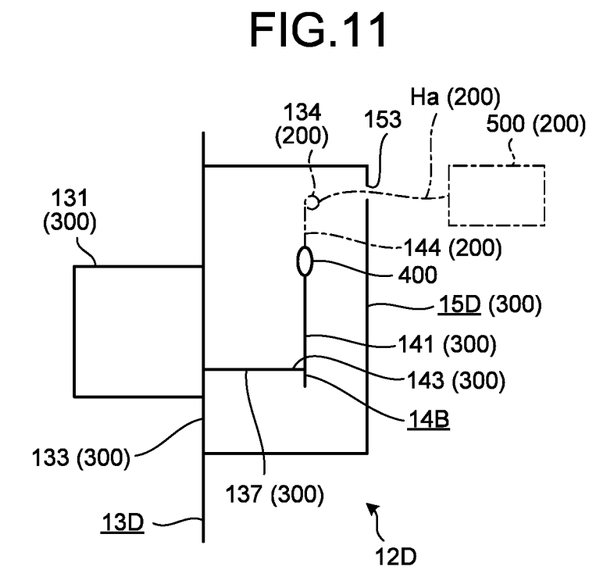
FIG. 11 is a diagram illustrating a fourth modification example of the embodiment.
Figure 12:
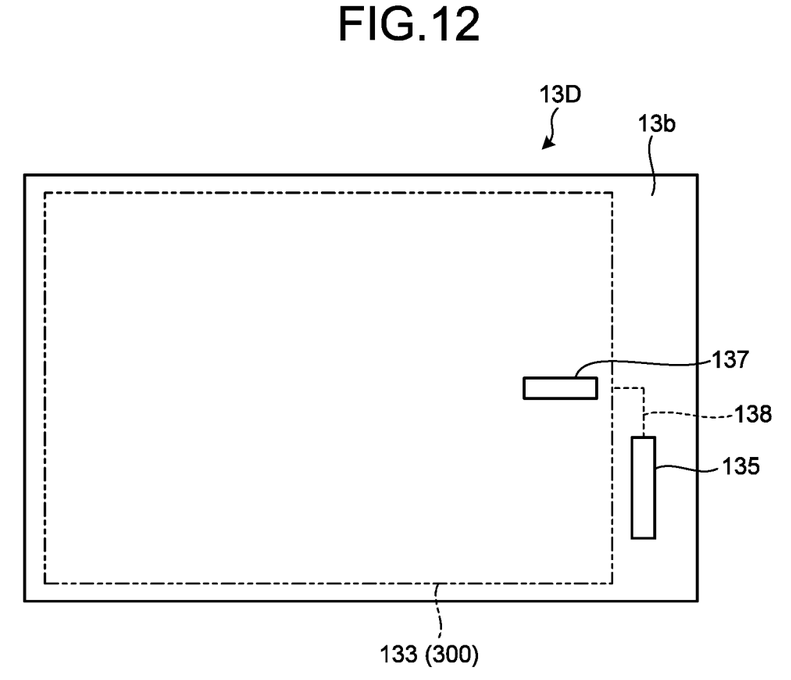
FIG. 12 is a diagram illustrating the fourth modification example of the embodiment.

FIGS. 11 and 12 are diagrams illustrating a fourth modification example of the embodiment. Specifically, FIG. 11 is a diagram corresponding to FIG. 5. In FIG. 11, as in FIG. 5, the patient circuit 300 and the insulation device 400 are indicated by solid lines, the secondary circuit 200 is illustrated by a one-dot chain line, and the second connection connector 135 is not illustrated. FIG. 12 is a diagram corresponding to FIG. 6.

In the above-described embodiment, instead of the receptacle module 12, a receptacle module 12D according to the fourth modification example illustrated in FIG. 11 may be adopted.

In the receptacle module 12D, unlike the receptacle module 12 described in the above-described embodiment, a receptacle substrate 13D and a patient substrate 14B which have different configurations from the receptacle substrate 13 and the patient substrate 14 is adopted, a shielding member 15D in which an opening 153 is formed in the shielding member 15 is adopted, and a mounting position of the shielding member 15D is different.

Specifically, in the receptacle substrate 13D, as illustrated in FIG. 11 or 12, the first secondary circuit unit 132 is omitted unlike the receptacle substrate 13 described in the above-described embodiment. As illustrated in FIG. 12, the first patient circuit unit 133 is provided on a region of the substantially entire surface of the receptacle substrate 13D. In the receptacle substrate 13D, the first connection connector 134 and the third connection connector 136 are omitted. The second connection connector 135 is mounted on the surface 13b of the receptacle substrate 13D in a region deviating from the first patient circuit unit 133 in a planar manner and is conducted to the first patient circuit unit 133 via the wiring pattern 138. That is, in the fourth modification example, the wiring pattern 138 described in the above-described embodiment is omitted. The fourth connection connector 137 is mounted on the surface 13b in a region overlapping the first patient circuit unit 133 in a planar manner and is conducted to the first patient circuit unit 133 as in the above-described embodiment.

The patient substrate 14B is the patient substrate 14B described in the above-described second modification example. In the patient substrate 14B, as illustrated in FIG. 11, the first connection connector 134 conducted to the second secondary circuit unit 144 is mounted in a region overlapping the second secondary circuit unit 144 in a planar manner. The secondary circuit substrate 500 is connected to the first connection connector 134 via the harness Ha or the like passing through the opening 153 formed in the shielding member 15 (FIG. 11). In the patient substrate 14B, as illustrated in FIG. 11, the fifth connection connector 142 is omitted.

As illustrated in FIG. 11, the shielding member 15D is mounted on the surface 13b of the receptacle substrate 13D in a region in which the opened portion is overlapped the first patient circuit unit 133 in a planar manner and is conducted to the ground line of the first patient circuit unit 133. That is, the shielding member 15D is set to the reference potential of the patient circuit 300. The shielding member 15D surrounds mainly the signal line of the first patient circuit unit 133, the second patient circuit unit 141, the second secondary circuit unit 144, the first, fourth, and sixth connection connectors 134, 137, and 143, and the insulation device 400 between the shielding member 15D and the receptacle substrate 13D (mainly the ground line (the shielding pattern according to the present disclosure) of the first patient circuit unit 133). On the other hand, the second connection connector 135 is located outside the shielding member 15D.

Even in the configuration in which the second secondary circuit unit 144 is provided in the patient substrate 14B as in the above-described fourth modification example, it is possible to obtain the same advantages as those of the above-described third modification example.

Figure 13:
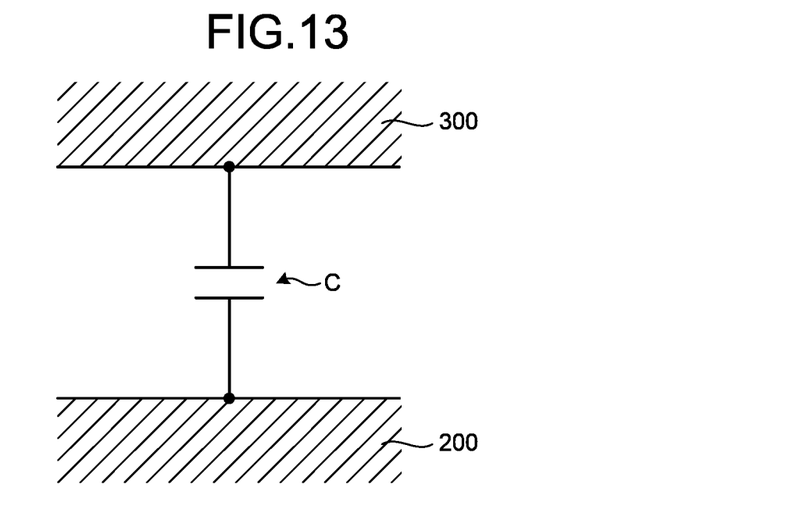
FIG. 13 is a diagram illustrating a fifth modification example of the embodiment.
Figure 14:
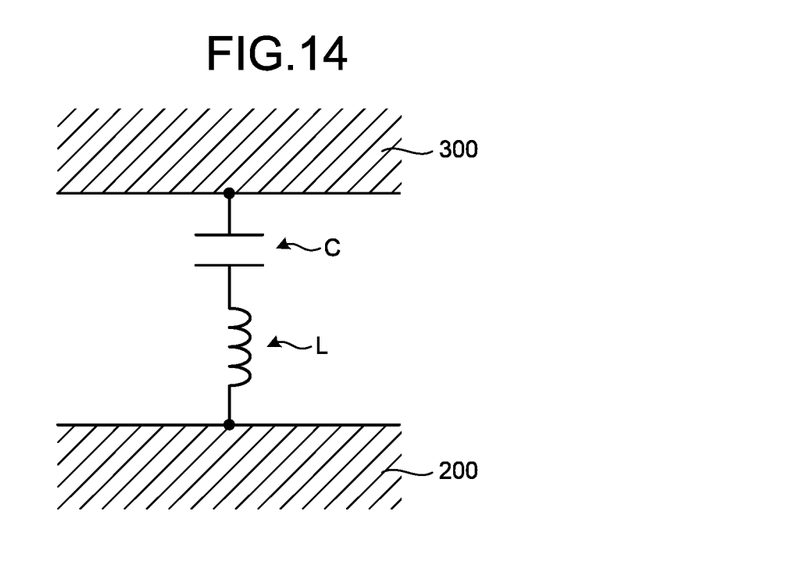
FIG. 14 is a diagram illustrating the fifth modification example of the embodiment.
Figure 15:
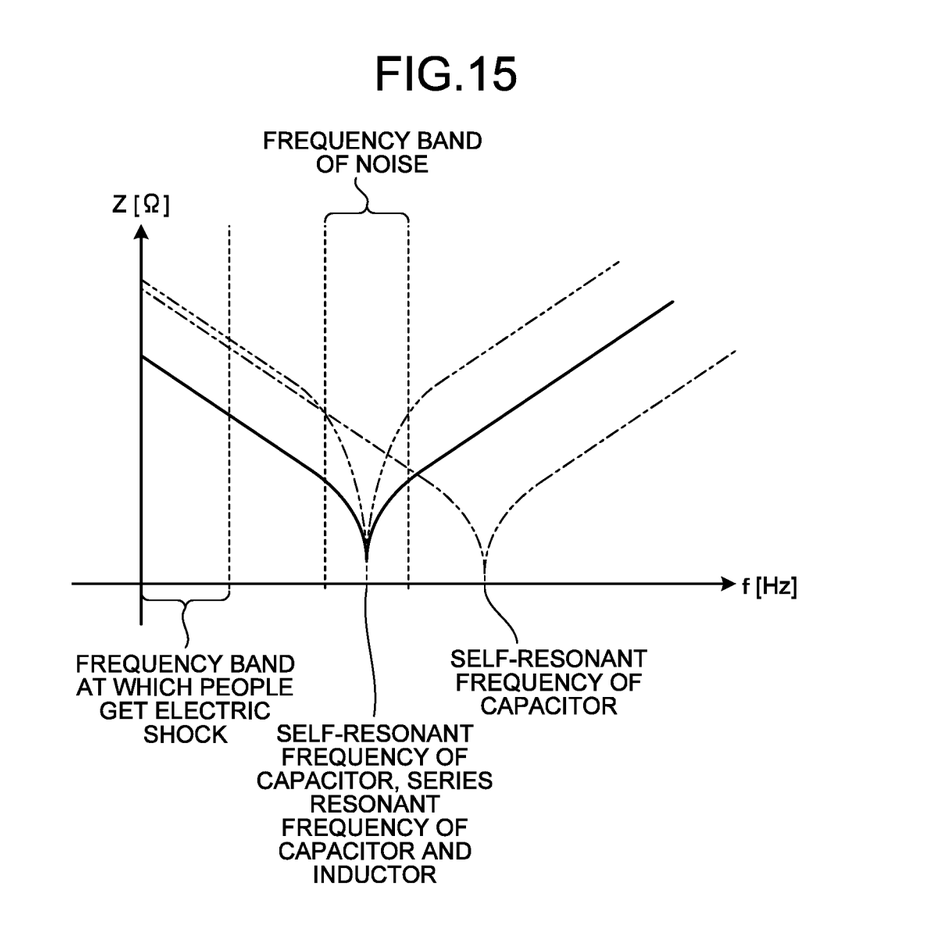
FIG. 15 is a diagram illustrating the fifth modification example of the embodiment.

FIGS. 13 to 15 are diagrams illustrating a fifth modification example of the embodiment.

In the above-described embodiment, as described in the fifth modification example, a configuration in which a reference potential of the secondary circuit 200 and a reference potential of the patient circuit 300 are connected via a single capacitor C (FIG. 13) or a configuration in which the reference potential of the secondary circuit 200 and the reference potential of the patient circuit 300 are connected via a capacitor C and an inductor L configuration (FIG. 14) connected to each other in series may be adopted to suppress mixing of noise or a leaked current.

Here, when the configuration in which the reference potential of the secondary circuit 200 and the reference potential of the patient circuit 300 are connected via the single capacitor C with a first capacitance which is a relatively large capacitance (FIG. 13: hereinafter referred to as a first configuration) is adopted, a self-resonant frequency of the capacitor C is located at a frequency band of target noise, as indicated by a solid line in FIG. 15. That is, it is possible to suppressing mixing of the noise. On the other hand, when the first configuration is adopted, impedance Z is relatively low in a low frequency band at which people get an electric shock, as indicated by a solid line in FIG. 15. That is, it is difficult to efficiently suppress a leaked current.

Accordingly, to increase the impedance Z at the low frequency band, a configuration in which the reference potential of the secondary circuit 200 and the reference potential of the patient circuit 300 are connected via a single capacitor C with a second capacitance which is a capacitance less than the first capacitance (FIG. 13: hereinafter referred to as a second configuration) is considered to be adopted. However, when the second configuration is adopted, the self-resonant frequency of the capacitor C may be higher than in the first configuration (indicated by a solid line in FIG. 15) and may deviate from the frequency band of the target noise, as indicated by a one-dot chain line in FIG. 15. That is, it is difficult to efficiently suppress mixing of noise.

In a configuration in which the reference potential of the secondary circuit 200 and the reference potential of the patient circuit 300 are connected via a capacitor C with the second capacitor and an inductor L (FIG. 14: hereinafter referred to as a third configuration), a series resonant frequency of the capacitor C and the inductor L may be located at a frequency band of the target noise without changing the impedance Z at the low frequency band, as indicated by a two-dot chain line in FIG. 15, compared to the second configuration (indicated by the one-dot chain line in FIG. 15). That is, it is possible to efficiently suppress both of mixing of the noise and the leaked current.

In the embodiment and the first to fifth modification examples described above, the first patient circuit unit 133 and the second patient circuit unit 141 have been adopted as patient circuit units according to the present disclosure, but the present disclosure is not limited thereto. A configuration in which the second patient circuit unit 141 (the patient substrates 14, 14B, and 14D) is omitted may be adopted. That is, all the patient circuit units according to the present disclosure may be provided in the receptacle substrates 13, 13C, and 13D.

In the embodiment and first to fifth modification examples described above, the medical device according to the present disclosure is configured as the endoscope device 1 in which the rigid endoscope (the insertion unit 2) is used, but the present disclosure is not limited thereto. For example, the medical device according to the present disclosure may be configured as an endoscope device in which a flexible endoscope is used, an ultrasonic diagnostic system in which an ultrasonic wave is used, an energy treatment system in which energy is given to a subject for treatment by the energy, or an X-ray device in which an X-ray is used.

In the receptacle module according to the present disclosure, the structure is adopted in which the shielding member is mounted on an opposite surface of a surface on which the receptacle is mounted in the receptacle substrate and the shielding member shields the patient circuit unit from an opposite side of the surface on which the receptacle is mounted.

Therefore, it is not necessary to separate the shielding member into two bodies or the like and it is possible to achieve simplification of the structure of the shielding member. By shielding the patient circuit unit by the shielding member, a part of the patient circuit unit (a part of a harness or the like) is not located outside the shielding member and it is possible to improve a shielding property of the patient circuit unit.

Accordingly, in the receptacle module according to the present disclosure, it is possible to obtain the advantage that the shielding property may be improved while simplifying the structure.

Since the medical device according to the present disclosure includes the above-described receptacle module, it is possible to obtain the same operational effects and the advantages as those of the above-described receptacle module.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A receptacle module for detachably connecting a connector of a distal end device coming into contact with or inserted into a subject, the receptacle module comprising:
    a receptacle substrate including
        a first surface on which a receptacle to which the connector is detachably connected is mounted, and
        a second surface on an opposite side of the first surface;
    a patient circuit unit conducted to the distal end device via the receptacle; and
    a conductive shielding mounted on the second surface and configured to shield the patient circuit unit from the opposite side, wherein
    the patient circuit unit includes a first patient circuit unit provided on the receptacle substrate and conducted to the receptacle,
    the receptacle substrate includes an insulation device configured to electrically insulate the first patient circuit unit from a secondary circuit unit connected to the first patient circuit unit via the insulation device, the secondary circuit unit surrounding the first patient circuit unit, and
    the conductive shielding is mounted on the receptacle substrate and set to a reference potential of the secondary circuit unit.

2. The receptacle module according to claim 1, further comprising a patient substrate disposed between the receptacle substrate and the conductive shielding and covered with the conductive shielding from the opposite side,
    wherein the patient circuit unit includes
        a first patient circuit unit provided on the receptacle substrate and conducted to the receptacle, and
        a second patient circuit unit provided on the patient substrate and conducted to the first patient circuit unit.

3. The receptacle module according to claim 2, wherein the receptacle substrate and the patient substrate are disposed at mutually facing postures.

4. The receptacle module according to claim 1, wherein the insulated transmitter is covered with the conductive shielding from the opposite side.

5. The receptacle module according to claim 1, wherein the receptacle substrate includes a conductive shielding pattern, and
    the patient circuit unit is surrounded by the shielding pattern and the conductive shielding.

6. The receptacle module according to claim 1, wherein the conductive shielding includes:
    a base provided on the receptacle substrate; and
    a shielding case mounted on the base.

7. A medical device comprising:
    the distal end device that comes into contact with or is inserted into the subject; and
    the receptacle module according to claim 1 to which the connector of the distal end device is detachably connected.

* * * * *